United States Patent [19]

Gubelmann et al.

[11] Patent Number: 5,288,906
[45] Date of Patent: Feb. 22, 1994

[54] PREPARATION OF P-AMINOPHENOLS

[75] Inventors: Michel Gubelmann, Paris; Christian Maliverney, Lyons, boyh of France

[73] Assignee: Rhone-Poulence Chimie, Courbevoie, France

[21] Appl. No.: 24,440

[22] Filed: Mar. 1, 1993

[30] Foreign Application Priority Data

Feb. 28, 1992 [FR] France .................. 9202346

[51] Int. Cl.$^5$ .......................................... C07C 209/36
[52] U.S. Cl. .................................. 564/144; 564/138; 564/418
[58] Field of Search ................. 564/418, 138, 144

[56] References Cited

U.S. PATENT DOCUMENTS

| 4,176,138 | 11/1979 | Sathe | 564/418 |
| 4,571,437 | 2/1986 | Caskey et al. | 564/418 |
| 4,885,389 | 12/1989 | Lee et al. | 564/418 |

Primary Examiner—Richard L. Raymond
Attorney, Agent, or Firm—Burns, Doane, Swecker & Mathis

[57] ABSTRACT

Optionally substituted p-aminophenol compounds, easily converted into the N-acylated derivatives thereof, are prepared by hydrogenating the corresponding nitrobenzene, in solution in a saturated aliphatic monocarboxylic acid, notably acetic acid, in the presence of an effective amount of a protonic acid.

20 Claims, No Drawings

PREPARATION OF P-AMINOPHENOLS

BACKGROUND OF THE INVENTION

1. Field of the Invention

The present invention relates to the preparation of p-aminophenols from the corresponding nitrobenzenes, and, more especially, to the preparation of p-aminophenolic compounds and N-acylated derivatives thereof that are optionally substituted on their respective aromatic nucleii.

The present invention more particularly relates to the preparation of p-aminophenol, a valuable compound economically, because it is a useful intermediate for the production of N-acetyl-p-aminophenol ("APAP").

2. Description of the Prior Art

It is known to this art to prepare p-aminophenols from phenylhydroxyl amines via the Bamberger Rearrangement (E. Bamberger, Ber., 27, 1347, 1548 (1894)).

Phenylhydroxyl amines are prepared by a careful reduction of nitrobenzene.

A direct route for the preparation of p-aminophenol entails the catalytic reduction of nitrobenzene. This reaction is carried out in an aqueous medium, in the presence of a strong acid, and in particular sulfuric acid, as well as a hydrogenation catalyst, generally platinum deposited onto a support.

p-Aminophenol production can be accompanied by the formation of byproducts such as aniline, 4-amino-4'-hydroxydiphenyl amine, 4-amino-4'-hydroxydiphenyl ether, 4,4'-dihydroxydiphenyl amine and 4,4'-diaminodiphenyl ether.

In order to limit the formation of byproducts, it is also known to this art to include additives in the process sequence, which are either catalyst poisons such as sulfur compounds (U.S. Pat. No. 4,571,437), or surfactants (U.S. Pat. No. 4,176,138).

The processes described in the aforesaid patents consequently require the use of supplementary additives.

SUMMARY OF THE INVENTION

Accordingly, a major object of the present invention is the provision of an improved process for the synthesis of optionally substituted p-aminophenols and N-acylated derivatives thereof, while minimizing the formation of byproducts without resorting to supplementary additives.

Briefly, the present invention features a process for the preparation of optionally substituted p-aminophenols from the corresponding nitrobenzenes, comprising hydrogenating such corresponding nitrobenzenes in solution in a saturated aliphatic monocarboxylic acid, notably acetic acid, and in the presence of an effective amount of a protonic acid.

DETAILED DESCRIPTION OF PREFERRED EMBODIMENTS OF THE INVENTION

More particularly according to the present invention, the subject process is applicable to any benzene compound bearing an $NO_2$ substituent, in which the position para to the $NO_2$ substituent is unsubstituted (free).

The process according to the invention is based on the phenomenon that the saturated aliphatic monocarboxylic acid serves both as a reaction solvent and as a nucleophilic agent involved in the Bamberger transposition, i.e., the transformation of the intermediate, namely, the conversion of a benzene compound bearing a hydroxylamine —NH—OH function into a benzene compound bearing an amino group and, in the para-position, an acyloxy group. After hydrolysis, the latter is converted into a benzene compound bearing an amino group and, in the para-position, a hydroxyl group, or, by transacetylation, is converted into an N-acylated p-aminophenolic compound.

The process of the present invention is conducted in a saturated aliphatic monocarboxylic acid.

Such monocarboxylic acids are liquid under the conditions of reaction and preferably liquid at ambient temperature. By "ambient temperature" are intended those temperatures ranging from 18° to 25° C.

These saturated aliphatic monocarboxylic acids are well known to this art and are abundantly described in the literature; compare, for example, the *Handbook of Chemistry and Physics*.

Exemplary thereof are acetic acid, propionic acid, butyric acid, isobutyric acid, pentanoic acid and 2-methylbutanoic acid. Acetic acid, however, is the preferred saturated aliphatic monocarboxylic acid.

In the event of preparation of p-aminophenol, which is the preferred compound that is produced according to the invention, acetic acid permits the transformation of the phenylhydroxyl amine into p-acetoxyaniline which upon hydrolysis thereof, is converted into p-aminophenol, or, by transacetylation, into N-acetyl-p-aminophenol.

The present invention, however, is not limited to this preferred embodiment. As indicated above, the invention is applicable to any benzene compound bearing an $NO_2$ group, with the position para thereto being unsubstituted.

Among such $NO_2$-substituted benzene compounds, those preferred have the general formula (I):

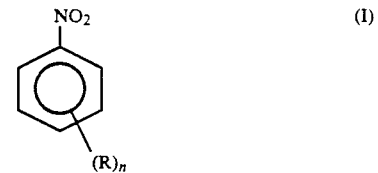

in which R is an alkyl or alkoxy radical having from 1 to 20 and preferably 1 to 6 carbon atoms, a perfluoroalkyl radical having from 1 to 4 carbon atoms, a halogen atom, preferably chlorine, bromine or fluorine, and n is a number equal to 0, 1, 2, 3 or 4, preferably 0,1 or 2.

It is also within the scope of the present invention to include other substituents on the aromatic nucleus of the starting nitro compounds, to the extent that they do not interfere with the reactions of the process. In particular, functional groups or halogen atoms may depend from the alkyl radicals borne by the benzene nucleus or for said alkyl radicals to be interrupted by a heteroatom such as oxygen, nitrogen or sulfur.

In the following description, the term "nitrobenzene" is used generically and designates both nitrobenzene and all $NO_2$-substituted benzene compounds and, in particular, those having the formula (I).

Exemplary nitrobenzenes having the formula (I) are nitrobenzene, o-nitrotoluene, m-nitrotoluene, 2,6-dimethyl-nitrobenzene, o-chloronitrobenzene, m-chloronitrobenzene, o-trifluoromethylnitrobenzene and m-trifluoromethylnitrobenzene.

The preferred starting compound used in the process according to the invention is nitrobenzene. It is possible to employ the commercially available product, which preferably has a purity greater than 99%. It is desirable to use a reagent containing less than 1% water.

The amount of the saturated aliphatic monocarboxylic acid employed as a reactant/reaction solvent can vary over wide limits. Typically, at least one mole thereof is used per mole of the nitrobenzene compound. Nonetheless, up to 500 moles of the saturated aliphatic monocarboxylic acid can be used, per mole of the nitrobenzene compound. Preferably, this amount ranges from 100 to 300 moles of said monocarboxylic acid per mole of the nitrobenzene.

As regards the preferred acetic acid used in the process according to the invention, glacial acetic acid, i.e., an acetic acid having a purity greater than 99.8%, is the more preferred. Because the acetic acid is used both as a reagent and as a reaction solvent, the amount used can vary very widely.

Thus, the amount of acetic acid used is at least 1 mole per mole of nitrobenzene. It is preferred to use a significant excess, such that the amount of acetic acid can also be as high as 500 moles per mole of nitrobenzene. Preferably, 100 to 300 moles of acetic acid are used per mole of nitrobenzene.

According to the invention a protonic acid having a pKa equal to or below 4.00 is also employed. preferably, a protonic acid having a Pka equal to or below 3.00 is used. The pKa is defined as being the ionic dissociation constant of the acid-base pair, when water is used as the solvent. For appropriate selection of an acid having a pKa as defined according to the invention, see, for example, *Handbook of Chemistry and Physics,* 66th edition, p. D-161 and D-162.

In respect of said protonic acid according to the invention, it is necessary to ensure that it has a nucleophilicity below that of the monocarboxylic acid, i.e., does not react on the aromatic nucleus.

Exemplary protonic acids according to the invention include the halogenated or non-halogenated mineral oxacids, such as sulfuric acid, chlorosulfonic acid, fluorosulfonic acid; phosphoric acids such as phosphoric acid, (2-ethylhexyl) phosphoric acid, (octylphenyl) phosphoric acid; phosphonic acids such as, e.g., (2-ethylhexyl) (2-ethylhexyl) phosphonic acid; perhalogenated or non-perhalogenated carboxylic acids such as formic acid, citric acid, trichloroacetic acid or trifluoroacetic acid. The halogenated or non-halogenated sulfonic acids are also very suitable. Exemplary of the latter are fluorosulfonic acid, chlorosulfonic acid, trifluoromethane sulfonic acid, methane sulfonic acid, ethane sulfonic acid, ethane disulfonic acid, benzene sulfonic acid, benzene disulfonic acids, toluene sulfonic acids, naphthalene sulfonic acids, naphthalene disulfonic acids and camphor sulfonic acids. Among these acids, sulfuric acid and the sulfonic acids are the preferred.

The amount of protonic acid, based on the number of equivalents of protons to the number of moles of nitrobenzene can vary over wide limits. Thus, the H+/nitrobenzene ratio can range from 0.5 to 5.0 and preferably from 0.5 to 3.0. The commercially available concentrated acids are the preferred.

The hydrogenation of the nitrobenzene is carried out in conventional manner, i.e., by contacting the nitrobenzene with hydrogen in the presence of a hydrogenation catalyst.

The catalyst can be at least one precious metal selected from among platinum and palladium. Such metal can be provided in finely divided state or can be deposited onto a support. Exemplary supports are charcoal, acetylene black, silica, alumina, zirconia, chromium oxide, bentonite, and the like.

The metal can be deposited onto the support in metallic state or in the form of a compound thereof, which will be reduced into the free metal in the presence of hydrogen. For example, a platinum and/or palladium oxide can be used. Among the aforementioned catalysts, the preferred catalyst is platinum deposited onto charcoal.

Preferably, the platinum and/or palladium is deposited onto a support and is generally deposited in an amount of 0.5% to 5% by weight of the catalyst.

The catalyst can be used in the form of powder, pellets or granules.

The amount of hydrogenation catalyst employed, expressed in gram atoms of precious metal per mole of nitrobenzene, advantageously ranges from $1.10^{-5}$ to $1.10^{-2}$, preferably from $5.10^{-5}$ to $1.10^{-3}$.

The process according to the invention is typically carried out at a temperature ranging from 50° to 200° C. and preferably from 80° to 150° C.

The reaction is conducted under a hydrogen pressure ranging from a pressure slightly above atmospheric pressure to a pressure of several hundred bars. Advantageously, the hydrogen pressure ranges from 1 to 20 bars and more preferably from 3 to 10 bars.

The reaction time can vary and is dependent on the nature of the protonic agent, the nitrobenzene concentration, the amount of catalyst, the pressure and the reaction temperature. It preferably ranges from 30 minutes to 5 hours.

From a practical standpoint, the reaction is easily carried out by introducing all the reagents at once into the reactor, namely, the nitrobenzene, the monocarboxylic acid, e.g., acetic acid, the protonic acid having a pKa equal to or less than 4.00 and the hydrogenation catalyst. The reaction medium is then heated to the desired temperature, while establishing a hydrogen atmosphere at the desired pressure, the reaction mixture being maintained under slight stirring at, for example, 500 to 1,000 r.p.m. When the reaction temperature is attained, stirring is increased up to approximately 2,000 r.p.m.

Stirring of the reaction medium is maintained throughout the reaction. At the end of the reaction, the spent catalyst and the p-aminophenolic compound produced are separated using conventional techniques.

Such final products are useful intermediates for the preparation of N-acylated p-aminophenolic compounds. This is the case during the preparation of N-acetyl-p-aminophenol, which is produced by the acetylation of p-aminophenol. The acetylation is preferably carried out using acetic anhydride.

According to the invention, the p-aminophenol compounds are prepared in major amounts. Under certain reaction conditions, for example using phosphoric acid as the protonic acid, the N-acyl derivatives are directly prepared in addition to the p-aminophenols.

In order to further illustrate the present invention and the advantages thereof, the following specific examples are given, it being understood that same are intended only as illustrative and in nowise limitative. In said examples to follow, PAP=p-aminophenol and APAP=N-acetyl-p-aminophenol.

$$\text{Conversion} = \frac{\text{number of moles of converted nitrobenzene}}{\text{number of moles of nitrobenzene introduced}}$$

$$\text{Yield} = \frac{\text{number of moles of PAP formed}}{\text{number of moles of nitrobenzene introduced}}$$

$$\text{Selectivity} = \frac{\text{number of moles of PAP + APAP formed}}{\text{number of moles of PAP + APAP + aniline + acetanilide formed}}$$

EXAMPLES 1-4

The operating procedure for all of the examples is given below:

Into a 70 cm³ reactor equipped with a Rushton turbine stirring system, a heating device, a temperature regulating device and a hydrogen feed pump were introduced the following reagents:

(i) 2.46 g of nitrobenzene (20 mmole),
(ii) 15 cm³ of glacial acetic acid,
(iii) 20 mmole of protonic acid,
(iv) $1.15 \cdot 10^{-5}$ gram atom of platinum deposited onto charcoal in an amount of 5% by weight.

The reaction medium was heated to a temperature of 120° C., while establishing a hydrogen atmosphere of 5 bars, with an initial stirring at 1,000 r.p.m. When a temperature of 120° C. was attained, stirring was increased to 2,000 r.p.m. The reaction time is reported in the following Table.

At the end of the reaction, the remaining reagents and the final products were determined by high performance liquid chromatography.

Four tests were carried out using different protonic acids. The results obtained are reported in the Table:

TABLE

| Examples | Strong acid | Time in hours | Conversion PhNO₂ (%) | Yield (%) | | | | Selectivity (%) |
| --- | --- | --- | --- | --- | --- | --- | --- | --- |
| | | | | PAP | APAP | PhNH₂ | PhNHAc | |
| 1 | H₃PO₄ | 6 h | 100 | 7.3 | 10.2 | 12.9 | 56.0 | 21 |
| 2 | PhSO₃H | 4 h | 100 | 17.4 | 0.1 | 45.3 | 11.7 | 24 |
| 3 | H₂SO₄ | 3 h | 45 | 30.2 | 0.1 | 14.2 | 0.2 | 68 |
| 4 | CF₃SO₃H | 1 h 45 min | 100 | 45.3 | 1.9 | 24.4 | 1.7 | 65 |

From the above Table, it will be seen that the best yields and selectivities were obtained when using sulfuric acid or trifluoromethane sulfonic acid as the protonic acid.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an optionally substituted p-aminophenol, comprising hydrogenating the corresponding nitrobenzene, in solution in a saturated aliphatic monocarboxylic acid, in the presence of an effective amount of a protonic acid.

2. The process as defined by claim 1, said nitrobenzene having the formula (I):

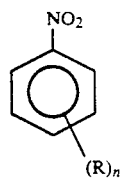

in which R is an alkyl or alkoxy radical having from 1 to 20 carbon atoms, a perfluoroalkyl radical having from 1 to 4 carbon atoms, or a halogen atom, and n is 0, 1, 2, 3 or 4.

3. The process as defined by claim 2, said nitrobenzene comprising nitrobenzene, o-nitrotoluene, m-nitrotoluene, 2,6-dimethyl nitrobenzene, o-chloronitrobenzene, m-chloronitrobenzene, o-trifluoromethyl nitrobenzene or m-trifluoromethyl nitrobenzene.

4. The process as defined by claim 1, said saturated aliphatic monocarboxylic acid comprising acetic acid, propionic acid, butyric acid, isobutyric acid, pentanoic acid or 2-methylbutanoic acid.

5. The process as defined by claim 4, said saturated aliphatic monocarboxylic acid comprising glacial acetic acid.

6. The process as defined by claim 1, wherein the amount of said saturated aliphatic monocarboxylic acid ranges from 1 to 500 moles thereof per mole of said nitrobenzene.

7. The process as defined by claim 6, wherein the amount of said saturated aliphatic monocarboxylic acid ranges from 100 to 300 moles thereof per mole of said nitrobenzene.

8. The process as defined by claim 1, said protonic acid having a pKa no greater than 4.00.

9. The process as defined by claim 8, said protonic acid having a pKa no greater than 3.00.

10. The process as defined by claim 8, said protonic acid comprising a halogenated or non-halogenated mineral oxacid, a phosphoric acid, a phosphonic acid, a perhalogenated or non-perhalogenated carboxylic acid, or a halogenated or non-halogenated sulfonic acid.

11. The process as defined by claim 10, said protonic acid comprising sulfuric, chlorosulfonic, fluorosulfonic, phosphoric, (2-ethylhexyl) phosphoric, (octylphenyl) phosphoric, (2-ethylhexyl) (2-ethylhexyl) phosphonic, formic, citric, trichloroacetic, trifluoroacetic, fluorosulfonic, chlorosulfonic, trifluoromethane sulfonic, methane sulfonic, ethane sulfonic, ethane disulfonic, benzene sulfonic, benzene disulfonic, toluene sulfonic, naphthalene sulfonic, naphthalene disulfonic or camphor sulfonic acid.

12. The process as defined by claim 11, said protonic acid comprising sulfuric acid or a sulfonic acid.

13. The process as defined by claim 1, wherein the amount of said protonic acid, based on the number of equivalents of protons to the number of moles of said nitrobenzene, ranges from 0.1 to 5.0.

14. The process as defined by claim 13, said amount ranging from 0.5 to 3.0.

15. The process as defined by claim 1, carried out in the presence of a catalytically effective amount of platinum or palladium.

16. The process as defined by claim 15, said platinum or palladium being deposited onto a support therefor.

17. The process as defined by claim 15, wherein the amount of said platinum or palladium catalyst ranges from $1.10^{-5}$ to $1.10^{-2}$ gram atoms thereof per mole of said nitrobenzene.

18. The process as defined by claim 1, carried out at a temperature ranging from 50° to 200° C.

19. The process as defined by claim 18, carried out under a hydrogen pressure ranging from 1 to 20 bars.

20. The process as defined by claim 1, further comprising N-acylating said optionally substituted p-aminophenol.

* * * * *